(12) United States Patent
Maubru et al.

(10) Patent No.: US 6,312,674 B1
(45) Date of Patent: *Nov. 6, 2001

(54) OXIDIZING COMPOSITION AND NOVEL METHOD FOR PERMING OR BLEACHING HAIR

(75) Inventors: Mireille Maubru, Chatou; Demarys Braida-Valerio, Paris, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,733
(22) PCT Filed: Oct. 21, 1996
(86) PCT No.: PCT/FR96/01644
  § 371 Date: Oct. 27, 1998
  § 102(e) Date: Oct. 27, 1998
(87) PCT Pub. No.: WO97/15273
  PCT Pub. Date: May 1, 1997

(30) Foreign Application Priority Data

Oct. 20, 1995 (FR) .................................................. 95 12386

(51) Int. Cl.$^7$ ............................... A61K 7/06; A61K 7/13; A61K 7/135; A61K 7/08
(52) U.S. Cl. ........................... 424/62; 424/401; 424/70.1; 424/70.2; 514/880; 132/202; 8/406
(58) Field of Search ..................... 424/401, 70.1, 424/70.14, 70.17, 70.2, 62; 514/880; 132/202; 8/406

(56) References Cited

U.S. PATENT DOCUMENTS

| | | | |
|---|---|---|---|
| 5,618,523 | 4/1997 | Zysman et al. | 424/70.1 |
| 5,700,456 | * 12/1997 | Dubief et al. | |
| 5,830,481 | * 11/1998 | Cauwet-Martin et al. | |

FOREIGN PATENT DOCUMENTS

| | | |
|---|---|---|
| 2 359 399 | 6/1975 | (DE) . |
| 3 843 892 | 6/1990 | (DE) . |
| 4 133 957 | 4/1993 | (DE) . |
| 4 402 929 | 6/1995 | (DE) . |
| 4 420 736 | 8/1995 | (DE) . |
| 4 424 530 | 1/1996 | (DE) . |
| 4 424 533 | 1/1996 | (DE) . |
| 0 227 994 | 7/1987 | (EP) . |
| 0 278 505 | 8/1988 | (EP) . |
| 0 500 437 | 8/1992 | (EP) . |
| 0 646 572 | 4/1995 | (EP) . |
| 0 647 617 | 4/1995 | (EP) . |
| 0 736 522 | 10/1996 | (EP) . |
| 2 586 913 | 3/1987 | (FR) . |
| 2 673 179 | 8/1992 | (FR) . |
| 2 679 770 | 2/1993 | (FR) . |
| 2 718 960 | 10/1995 | (FR) . |
| 63-169571 | 7/1988 | (JP) . |
| 94/07844 | 4/1994 | (WO) . |
| 94/08969 | 4/1994 | (WO) . |
| 94/08970 | 4/1994 | (WO) . |
| 94/10131 | 5/1994 | (WO) . |
| 94/24097 | 10/1994 | (WO) . |
| 95/16665 | 6/1995 | (WO) . |
| 95/23807 | 9/1995 | (WO) . |

OTHER PUBLICATIONS

English Language Derwent Abstract of FR 2 586 913.
English Language Derwent Abstract of FR 2 673 179.
English Language Derwent Abstract of DE 3 843 892.
English Language Derwent Abstract of DE 4 133 957.
English Language Derwent Abstract of DE 4 424 530.
English Language Derwent Abstract of DE 4 424 533.
English Language Derwent Abstract of DE 4 420 736.
English Language Derwent Abstract of DE 4 402 929.
English Language Derwent Abstract of JP 63–169571.
English Language Derwent Abstract of EP 0 647 617.
English Language Derwent Abstract of FR 2 679 770.
English Language Derwent Abstract of FR 2 718 960.
Kristi J. Robson et al., "6–Hydroxy–4–sphingenine in human epidermal ceramides", Journal of Lipid Research, vol. 35, 1994, pp. 2060–2068.
English Language Derwent Abstract of EP 0 736 552.
English Language Derwent Abstract of DE 2 359 399.

* cited by examiner

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

The present invention relates to a novel oxidizing composition for carrying out a bleaching or permanent reshaping operation on the hair, comprising, in a suitable cosmetic vehicle, at least one compound of ceramide type and at least one oxidizing agent. The invention also relates to novel processes for the bleaching and permanent reshaping of the hair, using the oxidizing composition defined above.

28 Claims, No Drawings

OXIDIZING COMPOSITION AND NOVEL METHOD FOR PERMING OR BLEACHING HAIR

This application is a 371 of PCT/FR96/01644, filed Oct. 21, 1996.

The invention relates to an oxidizing cosmetic composition in order to carry out a bleaching or permanent reshaping operation on the hair, and to processes for treating keratin substances, in particular the hair, in order to obtain permanent reshaping of these substances, in particular in the form of permanent-waved hair, or to obtain bleaching of these substances.

It is known that the most common technique for obtaining a permanent reshaping of the hair consists, in a first stage, in opening the —S—S-disulphide bonds of keratin (cystine) using a composition containing a suitable reducing agent (the reduction step) and then, after the hair thus treated has been rinsed, in reforming, in a second stage, the said disulphide bonds by applying to the hair, which has been placed under tension beforehand (curlers and the like), an oxidizing composition (the oxidation step, also known as the fixing step) in order finally to give the hair the desired shape. This technique thus makes it possible either to make the hair wavy or to straighten it or remove curls therefrom. The new shape given to the hair by a chemical treatment as above is considerably long-lasting and withstands, in particular, the action of washing with water or with shampoo, this being in contrast with simple standard techniques for temporary reshaping, such as hairsetting.

The reducing compositions which may be used to carry out the first step of a permanent-waving operation generally contain sulphites, bisulphites, alkylphosphines or, preferably, thiols as reducing agents. Among these reducing agents, those commonly used are cysteine and various derivatives thereof, cysteamine and derivatives thereof, thiolactic acid or thioglycolic acid, salts thereof and esters thereof, in particular glyceryl thioglycolate.

As regards the oxidizing compositions needed to carry out the fixing step, use is usually made, in practice, of compositions based on aqueous hydrogen peroxide solution or on alkaline bromates.

The problem with the technique of the permanent-waving compositions known to date is that applying them to the hair causes, in the long term, damage to the hair quality. The essential causes of this damage to the hair quality are a decrease in its cosmetic properties, such as its sheen, and a deterioration in its mechanical properties, more particularly a deterioration in its mechanical strength, due to swelling of the keratin fibres during the rinsing operation between the reduction step and the oxidation step, which may also be reflected by an increase in its porosity.

The hair is weakened and may become brittle during subsequent treatments such as blow-drying.

The same problem of damage to the keratin fibre is encountered during processes for dyeing or bleaching the hair. This hair is sensitized, that is to say damaged, to varying degrees by mechanical or chemical hair treatments, such as dyeing, bleaching and/or permanent-waving operations.

To solve this problem of damage to the hair quality, provision has been made to combine cationic polymers either with the reducing agents or with the oxidizing agents.

However, these solutions prove to be unsatisfactory since they do not entirely solve the problem of the decrease in the mechanical properties of the hair. In particular, in the case of a permanent reshaping treatment of the hair, this hair has an unsatisfactory feel and the curl hold is insufficient.

The aim of the present invention is, in particular, to solve the above problems.

More precisely, the aim of the invention is to provide a novel oxidizing composition which, when used in particular during the second stage of a permanent reshaping operation on the hair, makes it possible to limit, or even prevent altogether, the deterioration in the mechanical properties of the keratin substances, and more particularly breaking of the hair, and to obtain beautiful curls that withstand blow-drying and have good hold.

The aim of the invention is also to provide an oxidizing composition as above which makes it possible to improve the cosmetic properties, such as the softness and the ease of disentangling, of keratin fibres when they undergo, in particular, a permanent reshaping treatment.

Lastly, the aim of the present invention is to provide a novel process for the permanent reshaping of the hair using the oxidizing composition according to the invention.

Provision has been made, in Applications EP-A-0,647,617 and FR-A-2,673,179 in the name of the Applicant, to use specific ceramides in combination with lipids as an envelope for vesicles encapsulating water-soluble active substances, it being possible for these active substances to be, inter alia, oxidizing usagents, in order to protect the said active substances from the various harmful agents and from the reactive compounds which may be present in the composition.

Now, the Applicant has just discovered, entirely surprisingly, that the use of ceramide-type compounds in the oxidizing composition of a permanent reshaping process which is free of vesicles encapsulating an oxidizing agent makes it possible to obtain hair fibres which are in excellent condition at the end of the permanent-waving process.

The subject of the present invention is thus a novel oxidizing composition comprising, in a suitable cosmetic vehicle, i) at least one ceramide-type compound and ii) at least one oxidizing agent chosen from the group formed by aqueous hydrogen peroxide solution, alkaline bromates, persalts and polythionates or mixtures thereof, the said ceramide-type compound being present in the composition at a content ranging from 0.005% to 10% by weight relative to the total weight of the composition, the said composition being free of vesicles containing an oxidizing agent.

The subject of the present invention is also a novel process for treating keratin substances, in particular the hair, in order to obtain permanent reshaping of the hair, in particular in the form of permanent-waved hair, this process comprising the following steps: (i) a reducing composition is applied to the keratin substance to be treated, the keratin substance being placed under mechanical tension before, during or after the said application, (ii) the keratin substance is optionally rinsed, (iii) an oxidizing composition as defined above is applied to the optionally rinsed keratin substance, (iv) the keratin substance is optionally rinsed again.

The process according to the invention is particularly suitable for obtaining permanent-waved hair without the risk of deterioration of the keratin fibres. In particular, the process according to the invention limits breaking of the hair. Beautiful uniform curls are obtained, as well as better hold of the hairstyle. Hair treated according to the process of the invention feels pleasant when wet and is easier to style. The shape acquired by hair which has undergone the permanent reshaping treatment according to the invention also has good persistence over time with respect to shampooing.

The subject of the present invention is also a novel process for bleaching keratin substances, in particular the hair, comprising the following steps: i) an oxidizing composition according to the invention is applied to the keratin substance, this composition preferably comprising aqueous hydrogen peroxide solution alone or in the presence of persalts in alkaline medium, ii) the keratin substance thus treated is rinsed.

Other characteristics, aspects and advantages of the invention will emerge even more clearly on reading the detailed description which follows, as well as various concrete, but in no way limiting, examples intended to illustrate it.

Although the account which follows focuses essentially on the specific case of treatment of the hair, it will be noted here that the process according to the invention is applicable to any keratin substance in general, in particular eyelashes, moustaches, body hair, wool and the like.

Hereinabove and hereinbelow, the term vesicles is understood to refer to lipid spherules made of organized molecular layers containing an encapsulated aqueous phase, these layers being made of at least one ceramide-type compound combined with at least one other lipid compound.

According to the present invention, the term ceramide-type compounds is understood to refer to ceramides and/or glycoceramides and/or pseudoceramides. They are preferably chosen from natural or synthetic molecules corresponding to formula (I) below:

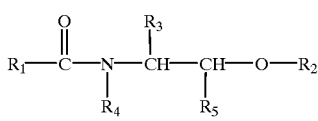

(I)

in which:
$R_1$ denotes:
either a linear or branched, saturated or unsaturated $C_1$–$C_{50}$, preferably $C_5$–$C_{50}$, hydrocarbon radical, it being possible for this radical to be substituted with one or more hydroxyl groups that are optionally esterified with an acid $R_7COOH$, $R_7$ being a saturated or unsaturated, linear or branched, optionally mono- or polyhydroxylated, $C_1$–$C_{35}$ hydrocarbon radical, it being possible for the hydroxyl(s) of the radical $R_7$ to be esterified with a saturated or unsaturated, linear or branched, optionally mono- or polyhydroxylated, $C_1$–$C_{35}$ fatty acid,
or a radical R"—(NR—CO)—R', R denotes a hydrogen atom or a mono- or polyhydroxylated, preferably monohydroxylated, $C_1$–$C_{20}$ hydrocarbon radical, R' and R" are hydrocarbon radicals the sum of whose carbon atoms is between 9 and 30, R' being a divalent radical,
or a radical $R_8$—O—CO—$(CH_2)_p$, $R_8$ denoting a $C_1$–$C_{20}$ hydrocarbon radical, p being an integer ranging from 1 to 12;
$R_2$ is chosen from a hydrogen atom, a radical of saccharide type, in particular a (glycosyl)$_n$, (galactosyl)$_m$ or sulphogalactosyl radical, a sulphate or phosphate residue, a phosphorylethylamine radical and a phosphorylethylammonium radical, in which n is an integer ranging from 1 to 4 and m is an integer ranging from 1 to 8;
$R_3$ denotes a hydrogen atom or a saturated or unsaturated, hydroxylated or non-hydroxylated $C_1$–$C_{33}$ hydrocarbon radical, it being possible for the hydroxyl(s) to be esterified with an inorganic acid or an acid $R_7COOH$, $R_7$ having the same meanings as above, it being possible for the hydroxyl(s) to be etherified with a (glycosyl)$_n$, (galactosyl)$_m$, sulphogalactosyl, phosphorylethylamine or phosphorylethylammonium radical, it also being possible for $R_3$ to be substituted with one or more $C_1$–$C_{14}$ alkyl radicals;
preferably, $R_3$ denotes a $C_{15}$–$C_{26}$ α-hydroxyalkyl radical, the hydroxyl group optionally being esterified with a $C_{16}$–$C_{30}$ α-hydroxy acid;
$R_4$ denotes a hydrogen atom, a methyl or ethyl radical, a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denotes a $C_1$–$C_{20}$ hydrocarbon radical, p being an integer ranging from 1 to 12,
$R_5$ denotes a hydrogen atom or a saturated or unsaturated, linear or branched, optionally mono- or polyhydroxylated $C_1$–$C_{30}$ hydrocarbon radical, it being possible for the hydroxyl(s) to be etherified with a (glycosyl)$_n$, (galactosyl)$_m$, sulphogalactosyl, phosphorylethylamine or phosphorylethylaammonium radical,
with the proviso that when $R_3$ and $R_5$ denote hydrogen or when $R_3$ denotes hydrogen and $R_5$ denotes methyl, then $R_4$ does not denote a hydrogen atom or a methyl or ethyl radical.

Among the compounds of formula (I) above, the ceramides and/or glycoceramides described by Downing in Journal of Lipid Research, Vol. 35, page 2060, 1994 or those described in French patent application FR-2,673,179, the teachings of which are included herein by way of reference, are preferred.

The ceramide-type compounds more particularly preferred according to the invention are the compounds of formula (I) for which $R_1$ denotes a saturated or unsaturated, optionally hydroxylated alkyl radical derived from $C_{14}$–$C_{22}$ fatty acids; $R_2$ denotes a hydrogen atom; and $R_3$ denotes a saturated, linear, optionally hydroxylated $C_{11}$–$C_{17}$ and preferably $C_{13}$–$C_{15}$ radical.

Such compounds are, for example:

2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol or mixtures of these compounds.

Specific mixtures may also be used, such as, for example, mixtures of ceramide(s) 2 and of ceramide(s) 5 according to the Downing classification.

Compounds of formula (I) for which $R_1$ denotes a saturated or unsaturated alkyl radical derived from fatty acids; $R_2$ denotes a galactosyl or sulphogalactosyl radical; and $R_3$ denotes a saturated or unsaturated $C_{12}$–$C_{22}$ hydrocarbon radical and preferably a —CH=CH—$(CH_2)_{12}$—$CH_3$ group, may also be used.

Ceramide-type compounds are described, for example, in patent applications DE 4,424,530, DE 4,424,533, DE 4,402,929, DE 4,420,736, WO 95/23807, WO 94/07844, EP-A-0, 646,572, WO 95/16665, FR-2,673,179, EP-A-0,227,994, WO 94/07844, WO 94/24097 and WO 94/10131, the teachings of which are included herein by way of reference.

For example, mention may be made of the product made of a mixture of glycoceramides, sold under the trade name Glycocer by the company Waitaki International Biosciences.

The compounds described in patent applications EP-A-0,227,994, EP-A-0,647,617, EP-A-0,736,522 and WO 94/07844 may also be used.

Such compounds are, for example, Questamide H, also known as bis(N-hydroxyethyl-N-cetyl)malonamide and sold by the company Quest, and cetylic acid N-(2-hydroxyethyl)-N-(3-cetyloxy-2-hydroxypropyl)amide.

N-Docosanoyl-N-methyl-D-glucamine as described in patent application WO 94/24097 may also be used.

The ceramide-type compound used in the present invention is preferably chosen from 2-N-oleoylaminooctadecane-1,3-diol, 2-N-[2-hydroxypalmitoyl]aminooctadecane-1,3-diol and N-stearoylphytosphingosine.

The ceramide(s) and/or glycoceramide(s) are present in the composition according to the invention at a content ranging from 0.005% to 10%, preferably ranging from 0.01% to 5%.

The oxidizing agent for the composition according to the invention is chosen from the group formed by aqueous hydrogen peroxide solution, alkaline bromates, persalts or polythionates or mixtures thereof, such as a mixture of alkaline bromate and of a persalt, or of a persalt and of aqueous hydrogen peroxide solution. The oxidizing agent for the compositions according to the invention is preferably aqueous hydrogen peroxide solution.

The aqueous hydrogen peroxide solution concentration may range from 0.5 to 40 volumes, preferably from 2 to 30 volumes. The alkaline bromate concentration is generally from 1 to 12% and the persalt concentration from 0.1 to 25%, by weight relative to the total weight of the oxidizing composition.

The pH of the entire oxidizing composition is preferably between 1 and 13, and even more preferably between 2 and 12.

This pH may be obtained and/or adjusted conventionally by adding either basifying agents such as, for example, aqueous ammonia, monoethanolamine, diethanolamine, triethanolamine, isopropanolamine, propane-1,3-diamine, an ammonium or alkaline carbonate or bicarbonate, an organic carbonate such as guanidine carbonate, or alternatively an alkaline hydroxide, it being possible, obviously, for all of these compounds to be taken alone or as a mixture, or acidifying agents such as, for example, hydrochloric acid, acetic acid, lactic acid or boric acid.

The oxidizing composition may be in the form of a lotion which may or may not be thickened, a cream, a gel or any other suitable form and may contain additives which are known for their use in oxidizing compositions for the bleaching or permanent reshaping of the hair. The composition may be in the form of a shampoo.

The oxidizing composition may also, in particular in the case of bleaching, be in the form of two parts to be mixed together at the time of use, one of these two parts containing alkaline agents and being in solid or liquid form.

The oxidizing composition may also contain cosmetic additives that are well known for this type of composition, such as basifying or acidifying agents, preserving agents, sequestering agents, cations, opacifiers and optionally a cationic polymer.

A second subject of the present invention is a process for the permanent reshaping of keratin fibres, and in particular the hair, using the composition defined above as oxidizing composition.

The first step of this process consists in applying a reducing composition to the hair. This application is carried out lock by lock or all at once.

The reducing composition comprises at least one reducing agent which may be chosen, in particular, from thioglycolic acid, cysteine, cysteamine, glyceryl thioglycolate, thiolactic acid or salts of thiolactic acid or of thioglycolic acid.

The usual step of placing the hair under tension in a shape corresponding to the desired final shape for this hair (for example curls) may be carried out by any means, in particular mechanical means, which is suitable and known per se for maintaining the hair under tension, such as, for example, rollers, curlers and the like.

The hair may also be placed in shape without the aid of external means, but simply with the fingers.

Before carrying out the following optional rinsing step, the hair onto which the reducing composition has been applied should, conventionally, be left to stand for a few minutes, generally between 5 minutes and one hour, preferably between 10 and 30 minutes, in order to give the reducing agent plenty of time to act properly on the hair. This waiting phase preferably takes place at a temperature ranging from 35° C. to 45° C., preferably while also protecting the hair with a hood.

In the second, optional, step of the process (step (ii)), the hair impregnated with the reducing composition is then rinsed thoroughly with an aqueous composition.

Next, in a third step (step (iii)), the oxidizing composition of the invention is applied to the hair thus rinsed, with the aim of fixing the new shape given to the hair.

As in the case of the application of the reducing composition, the hair onto which the oxidizing composition has been applied is then, conventionally, left in a waiting or standing phase which lasts a few minutes, generally between 3 and 30 minutes, preferably between 5 and 15 minutes.

The vehicle for the reducing and oxidizing compositions used according to the invention is preferably water or an aqueous-alcoholic solution of a lower alcohol such as ethanol, isopropanol or butanol.

The aqueous hydrogen peroxide solution may be stabilized, for example, with phenacetin, acetanilide, mono- and trisodium phosphates or with 8-hydroxy-quinoline sulphate, or stannates, including sodium stannate.

If the hair tension was maintained by external means, these means (rollers, curlers and the like) may be removed from the hair before or after the fixing step.

Lastly, in the final step of the process according to the invention (step (iv)), which is also optional, the hair impregnated with the oxidizing composition is rinsed thoroughly, generally with water.

Hair which is soft and easy to disentangle is finally obtained. The hair is wavy.

The oxidizing composition according to the invention may also be used in a process for bleaching keratin fibres, and in particular the hair.

The bleaching process according to the invention comprises a step of applying an oxidizing composition according to the invention to the keratin fibres, this composition preferably comprising aqueous hydrogen peroxide solution in alkaline medium. Conventionally, a second step of the bleaching process according to the invention is a step of rinsing the keratin fibres.

Concrete examples illustrating the invention will now be given.

Hereinbelow and hereinabove, except where otherwise mentioned, the percentages are expressed on a weight basis.

EXAMPLE 1

The Applicant carried out a comparative test in order to demonstrate the improvement afforded as regards the mechanical strength of keratin fibres by adding ceramides to an oxidizing composition for a treatment process for the permanent reshaping of keratin fibres.

The oxidizing composition A below, also known as the fixer, in accordance with the invention was prepared:

Fixer A

| | |
|---|---|
| - N-oleyldihydrosphingosine (ceramide) | 1% |
| - 200-volume aqueous hydrogen peroxide solution | 4.8% |
| - lauryldimethylamine oxide as an aqueous solution containing 30% AM | 1% |
| - citric acid | qs pH = 3 |
| - demineralized water | qs 100% |

A comparative oxidizing composition B, of the same composition as A but containing no N-oleyldihydrosphingosine, was also prepared.

The above oxidizing compositions were prepared by simple mixing, after dissolution or dispersion and heating of the ceramide.

In order to compare the two oxidizing compositions during a permanent reshaping treatment of the hair, a reducing composition of the following composition was prepared:

Reducing Composition

| | |
|---|---|
| - cocoylamidopropylbetaine/glyceryl monolaurate mixture containing 30% AM | 1.4% gross |
| - thioglycolic acid | 6.7% |
| - ammonium bicarbonate | 5.1% |
| - sequestering agent | 0.2% |
| - aqueous ammonia containing 20% $NH_3$ | 6.2% |
| - demineralized water | qs 100% |

The reducing composition was prepared by simple mixing.

The reducing composition was then applied to locks of sensitized hair, in a ratio of 2 g of bath/g of hair. The term sensitized hair is understood to refer to hair damaged to varying degrees by the action of atmospheric agents and/or of mechanical or chemical hair treatments, such as dyeing, bleaching and/or permanent-waving operations. After leaving the composition to stand on the hair for 10 minutes, the hair was rinsed with water.

Each of the compositions A and B was then applied to the rinsed hair, in a ratio of 2 g of bath/g of hair. After leaving the composition to stand on the hair for 5 minutes, the hair was rinsed and then dried.

The ability of each composition to limit the deterioration of the keratin fibres was evaluated according to the following procedure: for each head of hair pretreated as indicated above with composition A or B, three locks of hair were moistened and then placed on a metal support in order to hold the hair at the root. Blow-drying was then carried out as uniformly as possible.

The hair broken during the blow-drying was meticulously collected on the brush, introduced into a Petri dish and then weighed after conditioning for 12 hours at a relative humidity of 50%±2% and at a temperature of 20° C.±2° C.

The results obtained are given in Table (I) below:

TABLE (I)

| Formula | Amount of broken hair mg/g |
|---|---|
| Composition A (invention) | 17.8 ± 3.0 |
| Composition B (comparative) | 28.1 ± 3.2 |

These results show clearly that the introduction of a ceramide into an oxidizing composition for a permanent reshaping process greatly limits the deterioration of keratin fibres.

EXAMPLE 2

A concrete example of an oxidizing composition for bleaching the hair is given below:

| | |
|---|---|
| - potassium persulphate | 27% |
| - sodium persulphate | 23% |
| - diammonium phosphate | 9% |
| - silica | 15% |
| - sodium metasilicate | 15% |
| - magnesium carbonate | 6% |
| - hydroxyethylcellulose | 2.5% |
| - N-oleyldihydrosphingosine | 0.5% |
| - sequestering agent | 2% |

What is claimed is:

1. An oxidizing composition comprising, in a suitable cosmetic vehicle:
    at least one ceramide compound selected from compounds of formula (I):

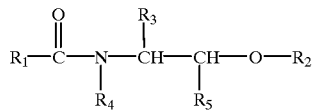

in which:
    $R_1$ denotes
        a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or
        a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
        a radical $R_8$—O—CO—$(CH_2)_p$, in which $R_8$ denotes a $C_1$–$C_{20}$ hydrocarbon radical and p is an integer ranging from 1 to 12;
    $R_2$ denotes a hydrogen atom, a saccharide radical, a sulphate residue, a phosphate residue, a phosphorylethylamine radical, or a phosphorylethylammonium radical;
    $R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or phosphorylethylammonium radical,
    and further wherein $R_3$ is optionally substituted with one or more $C_1$–$C_{14}$ alkyl radicals, wherein n is an integer ranging from 1 to 4 and m is an integer ranging from 1 to 8;

R₄ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and at least one oxidizing agent selected from an aqueous hydrogen peroxide solution, alkaline bromates, persalts, and polythionates, wherein said oxidizing composition does not contain a cationic polymer or vesicles encapsulating an oxidizing agent.

2. An oxidizing composition according to claim 1, wherein said at least one ceramide compound is present in an amount ranging from 0.005 to 10% by weight relative to the total weight of said composition.

3. An oxidizing composition according to claim 2, wherein said at least one ceramide compound is present in an amount ranging from 0.01 to 5% by weight relative to the total weight of said composition.

4. An oxidizing composition according to claim 1, wherein R in said radical R"—(NR—CO)—R' denotes a monohydroxylated $C_1$–$C_{20}$ hydrocarbon radical.

5. An oxidizing composition according to claim 1, wherein $R_2$ is selected from a (glycosyl)$_n$ radical, a (galactosyl)$_m$ radical, or a sulphogalactosyl radical, wherein n is an integer ranging from 1 to 4 and m is an integer ranging from 1 to 8.

6. An oxidizing composition according to claim 1, wherein said at least one ceramide compound is selected from compounds of formula (I) in which $R_1$ denotes a saturated or unsaturated, optionally hydroxylated alkyl radical derived from $C_{14}$–$C_{22}$ fatty acids; $R_2$ denotes hydrogen; and $R_3$ denotes a saturated, linear, optionally hydroxylated $C_{11}$–$C_{17}$ radical.

7. An oxidizing composition according to claim 6, wherein $R_3$ denotes a saturated, linear, optionally hydroxylated $C_{13}$–$C_{15}$ radical.

8. An oxidizing composition according to claim 1, wherein said at least one ceramide compound is selected from:

N-stearoylphytosphingosine
2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol, and
2-N-palmitoylaminohexadecane-1,3-diol.

9. An oxidizing composition according to claim 8, wherein said at least one ceramide compound is N-stearoylphytosphingosine.

10. An oxidizing composition according to claim 8, wherein said at least one ceramide compound is selected from 2-N-oleoylaminooctadecane-1,3-diol, 2-N-(2-hydroxypalmitoyl)aminooctadecane-1,3-diol, and N-stearoylphytosphingosine.

11. An oxidizing composition according to claim 1, wherein said at least one oxidizing agent is an aqueous hydrogen peroxide solution.

12. An oxidizing composition according to claim 11, wherein said aqueous hydrogen peroxide solution concentration ranges from 0.5 to 40 volumes.

13. An oxidizing composition according to claim 12, wherein said aqueous hydrogen peroxide solution concentration ranges from 2 to 30 volumes.

14. A process for treating a keratin substance comprising:

applying a reducing composition to said keratin substance, wherein said keratin substance has been placed under tension before, during or after said applying step, optionally rinsing said keratin substance, applying to said keratin substance an oxidizing composition comprising, in a suitable cosmetic vehicle, at least one ceramide compound selected from compounds of formula (I):

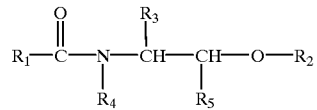

$R_1$ denotes a linear or branched, saturated or unsaturated, $C_1$–$C_{50}$ hydrocarbon radical, optionally substituted with at least one hydroxyl group and said at least one hydroxyl group is optionally esterified with an acid $R_7$COOH, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, la phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7$COOH, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or phosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2CHOH$—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and at least one oxidizing agent selected from aqueous hydrogen peroxide solution, alkaline bromates, persalts, and polythionates, wherein said oxidizing composition does not contain a cationic polymer or vesicles encapsulating an oxidizing agent, and optionally rinsing said keratin substance.

15. A process according to claim 14, wherein said keratin substance is human hair.

16. A process according to claim 15, wherein said process obtains permanent reshaping of said human hair.

17. A process for bleaching a keratin substance comprising:

applying to said keratin substance an oxidizing composition comprising, in a suitable cosmetic vehicle, at least one ceramide compound selected from compounds of formula (I):

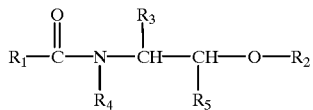

in which:
$R_1$ denotes
a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or phosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl )$_n$, (galactosyl )$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and at least one oxidizing agent selected from aqueous hydrogen peroxide solution, alkaline bromates, persalts, and polythionates, wherein said oxidizing composition does not contain a cationic polymer or vesicles encapsulating an oxidizing agent, and rinsing said keratin substance.

18. A process according to claim 17, wherein said keratin substance is hair.

19. An oxidizing composition according to claim 1, wherein for $R_1$, said linear or branched, saturated or unsaturated hydrocarbon radical is a $C_5$–$C_{50}$ hydrocarbon radical.

20. A process according to claim 15 wherein said process obtains permanent-waving of said human hair.

21. An oxidizing composition comprising, in a suitable cosmetic vehicle:

a) at least one ceramide compound selected from compounds of formula

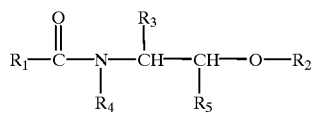

in which:
$R_1$ denotes
a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalelit radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a $(glycosyl)_n$, $(galactosyl)_m$, sulphogalactosyl, phosphorylethylamine or phosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a $(glycosyl)_n$, $(galactosyl)_m$, sulphogalactosyl, hosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and b) at least one oxidizing agent selected from an aqueous hydrogen peroxide solution, alkaline bromates, persalts, and polythionates, wherein said oxidizing composition does not contain vesicles encapsulating an oxidizing agent, and further wherein said at least one ceramide compound is not N-oleyidihydrosphingosine.

22. A process for treating a keratin substance comprising:

a) applying a reducing composition to said keratin substance, wherein said keratin substance has been placed under tension before, during or after said applying step;

b) optionally rinsing said keratin substance;

c) applying to said keratin substance an oxidizing composition comprising, in a suitable cosmetic vehicle, at least one ceramide compound selected from compounds of formula (I):

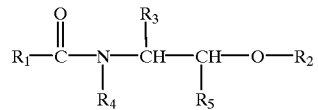

in which:

$R_1$ denotes a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a $(glycosyl)_n$, $(galactosyl)_m$, sulphogalactosyl, phosphorylethylamine or hosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a $(glycosyl)_n$, $(galactosyl)_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical;

and at least one oxidizing agent selected from aqueous hydrogen peroxide solution, alkaline bromates, persals, and polythionates, wherein said oxidizing composition does not contain vesicles encapsulating an oxidizing, and further wherein said at least one ceramide compound is not N-oleyidihydrosphingosine, and d) optionally rinsing said keratin substance.

23. A process for bleaching a keratin substance comprising:
a) applying to said keratin substance an oxidizing composition comprising, in a suitable cosmetic vehicle, at least one ceramide compound selected from compounds of formula (I):

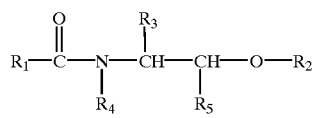

in which:
$R_1$ denotes
a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or
a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
a radical $R_8$—O—CO—$(CH_2)_p$, in which $R_8$ denotes a $C_1$–$C_{20}$ hydrocarbon radical and p is an integer ranging from 1 to 12;
$R_2$ denotes a hydrogen atom, a saccharide radical, a sulphate residue, a phosphate residue, a phosphorylethylamine radical, or a phosphorylethylammonium radical;
$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or hosphorylethylammonium radical,
and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;
$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and at least one oxidizing agent selected from aqueous hydrogen peroxide solution, alkaline bromates, persals, and polythionates, wherein said oxidizing composition does not contain vesicles encapsulating an oxidizing agent, and further wherein said at least one ceramide compound is not N-oleyldihydrosphingosine, and b) rinsing said keratin substance.

24. An oxidizing composition comprising, in a suitable cosmetic vehicle:
a) at least one ceramide compound selected from compounds of formula

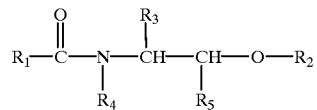

in which:
$R_1$ denotes
a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or
a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
a radical $R_8$—O—CO—$(CH_2)_p$, in which $R_8$ denotes a $C_1$–$C_{20}$ hydrocarbon radical and p is an integer ranging from 1 to 12;
$R_2$ denotes a hydrogen atom, a saccharide radical, a sulphate residue, a phosphate residue, a phosphorylethylamine radical, or a phosphorylethylammonium radical;
$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or phosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—$CHOH$—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and b) at least one oxidizing agent selected from an aqueous hydrogen peroxide solution, alkaline bromates, persalts, and polythionates, wherein said oxidizing composition does not contain vesicles encapsulating an oxidizing agent, and further wherein said oxidizing composition does not contain a cationic polymer containing primary, secondary, tertiary or quaternary amine groups in the main polymer.

25. A process for treating a keratin substance comprising:

a) applying a reducing composition to said keratin substance, wherein said keratin substance has been placed under tension before, during or after said applying step;

b) optionally rinsing said keratin substance;

c) applying to said keratin substance an oxidizing composition comprising, in a suitable cosmetic vehicle, at least one ceramide compound selected from compounds of formula (I):

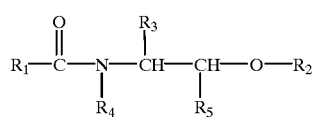

$R_1$ denotes a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or hosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—$CHOH$—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical;

and at least one oxidizing agent selected from aqueous hydrogen peroxide solution, alkaline bromates, persalts, and polythionates, wherein said oxidizing composition does not contain vesicles encapsulating an oxidizing agent, and further wherein said oxidizing composition does not contain a cationic polymer containing primary, secondary, tertiary or quaternary amine groups in the main polymer, and d) optionally rinsing said keratin substance.

26. A process for bleaching a keratin substance comprising:

a) applying to said keratin substance an oxidizing composition comprising, in a suitable cosmetic vehicle, at least one ceramide compound selected from compounds of formula (I):

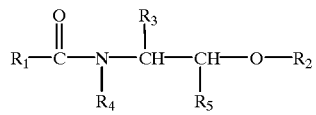

in which:

$R_1$ denotes
- a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or
- a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
- a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or hosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and at least one oxidizing agent selected from aqueous hydrogen peroxide solution, alkaline bromates, persalts, and polythionates, wherein said oxidizing composition does not contain vesicles encapsulating an oxidizing agent, and further wherein said oxidizing composition does not contain a cationic polymer containing primary, secondary, tertiary or quaternary amine groups in the main polymer, and b) rinsing said keratin substance.

27. An oxidizing composition comprising, in a suitable cosmetic vehicle:

a) at least one ceramide compound selected from compounds of formula (I):

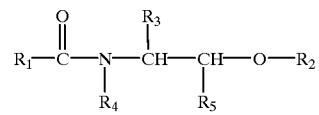

in which:

$R_1$ denotes
- a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or
- a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
- a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or hosphorylethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, hosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical; and b) at least one oxidizing agent selected from an aqueous hydrogen peroxide solution, alkaline bromates, persalts, and polythionates, wherein said oxidizing composition does not contain vesicles encapsulating an oxidizing agent, and further wherein said oxidizing composition is a fixer composition for the permanent reshaping of keratin fibres.

28. A process for permanently reshaping a keratin substance comprising:

a) applying a reducing composition to said keratin substance, wherein said keratin substance has been placed under tension before, during or after said applying step, b) optionally rinsing said keratin substance, c) applying to said keratin substance a fixer composition comprising, in a suitable cosmetic vehicle, at least one ceramide compound selected from compounds of formula (I):

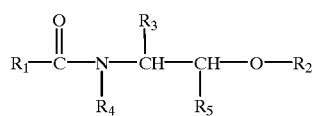

in which:
$R_1$ denotes
a linear or branched, saturated or unsaturated, $C_1$–$C_{50}$ hydrocarbon radical, optionally substituted with at least one hydroxyl group and said at least one hydroxyl group is optionally esterified with an acid $R_7COOH$, wherein $R_7$ is a saturated or unsaturated, linear or branched, optionally mono- or polyhydroxylated $C_1$–$C_{35}$ hydrocarbon radical, wherein said at least one hydroxyl group of radical $R_7$ is optionally esterified with a saturated or unsaturated, linear or branched, optionally mono- or polyhydroxylated $C_1$–$C_{35}$ fatty acid, or a radical R"—(NR—CO)—R', wherein R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or a radical $R_8$—O—CO—$(CH_2)_p$, in which $R_8$ denotes a $C_1$–$C_{20}$ hydrocarbon radical and p is an integer ranging from 1 to 12;

$R_2$ denotes a hydrogen atom, a saccharide radical, a sulphate residue, a phosphate residue, a phosphorylethylamine radical, or a phosphorylethylammonium radical;

$R_3$ denotes a hydrogen atom or a saturated or unsaturated, optionally mono- or polyhydroxylated $C_1$–$C_{33}$ hydrocarbon radical, wherein said hydroxyl radical(s) is optionally esterified with an inorganic acid or with an acid $R_7COOH$, wherein $R_7$ is a saturated or unsaturated, linear or branched, optionally mono- or polyhydroxylated $C_1$–$C_{35}$ fatty acid, and wherein said hydroxyl radical(s) of said $C_1$–$C_{35}$ fatty acid is optionally etherified with a (glycosyl)$_n$, (galactosyl)$_m$, sulphogalactosyl, phosphorylethylamine or hosphoryiethylammonium radical, and further wherein $R_3$ is optionally substituted with one or more $C_1$–$C_{14}$ alkyl radicals, wherein n is an integer ranging from 1 to 4 and m is an integer ranging from 1 to 8;

$R_4$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_6$ in which $R_6$ denotes a $C_{10}$–$C_{26}$ hydrocarbon radical or a radical $R_8$—O—CO—$(CH_2)_p$, $R_8$ denoting a $C_1$–$C_{20}$ hydrocarbon radical and p being an integer ranging from 1 to 12;

$R_5$ denotes a hydrogen atom or a saturated or unsaturated, linear or branched, optionally mono- or polyhydroxylated $C_1$–$C_{30}$ hydrocarbon radical, wherein said hydroxyl radical(s) is optionally etherified with a (glycosyl)$_n$, (galactosyl)$_m$, sulphogalactosyl, phosphorylethylamine or phosphorylethylammonium radical, wherein n is an integer ranging from 1 to 4 and m is an integer ranging from 1 to 8; and further wherein when $R_3$ and $R_5$ denote hydrogen or when $R_3$ denotes hydrogen and $R_5$ denotes methyl, then $R_4$ does not denote hydrogen or a methyl or ethyl radical;

and at least one oxidizing agent selected from aqueous hydrogen peroxide solution, alkaline bromates, persaits, and polythionates, wherein said fixer composition does not contain vesicles encapsulating an oxidizing agent, and c) optionally rinsing said keratin substance.

* * * * *

UNITED STATES PATENT AND TRADEMARK OFFICE
CERTIFICATE OF CORRECTION

PATENT NO. : 6,312,674 B1
DATED : November 6, 2001
INVENTOR(S) : Mireille Maubru et al.

It is certified that error appears in the above-identified patent and that said Letters Patent is hereby corrected as shown below:

Title page,
Item [54], in the title, "OXIDIZING COMPOSITION AND NOVEL METHOD FOR PERMING OR BLEACHING HAIR" should read -- OXIDIZING COMPOSITIONS AND METHOD FOR PERMING OR BLEACHING --.

Column 10,
Line 32, before "$R_1$ denotes" insert -- in which: -- and a line break.
Line 54, "la phosphate" should read -- a phosphate --.

Column 12,
Line 26, $C_1$-$C_{20}$hydrocarbon" should read -- $C_1$ $C_{20}$ hydrocarbon --.

Column 13,
Line 14, "divalelit" should read -- divalent --.
Line 49, "hosphorylethylamine" should read -- phosphorylethylamine --.
Line 62, "N-oleyidihydrosphingosine" should read -- N-oleyldihydrosphingosine --.

Column 14,
Line 49, "hosphorylethylammonium" should read -- phosphorylethylammonium --.

Column 15,
Line 13, "N-oleyidihydrosphingosine" should read -- N-oleyldihydrosphingosine --.
Line 63, "hosphorylethylammonium" should read -- phosphorylethylammonium --.

Column 17,
Line 59, before "$R_1$ denotes" insert -- in which: -- and a line break.

Column 18,
Line 9, "divalerit" should read -- divalent --.
Line 26, "hosphorylethylammonium" should read -- phosphorylethylammonium --.

Column 19,
Line 43, "hosphorylethylammonium" should read -- phosphorylethylammonium --.

Column 20,
Line 58, "hosphorylethylammonium" should read -- phosphorylethylammonium --.

UNITED STATES PATENT AND TRADEMARK OFFICE
CERTIFICATE OF CORRECTION

PATENT NO.   : 6,312,674 B1
DATED        : November 6, 2001
INVENTOR(S)  : Mireille Maubru et al.

It is certified that error appears in the above-identified patent and that said Letters Patent is hereby corrected as shown below:

<u>Column 21,</u>
Line 9, "hosphorylethylamine" should read -- phosphorylethylamine --.

<u>Column 22,</u>
Line 22, "hosphoryiethylammonium" should read -- phosphorylethylammonium --.

Signed and Sealed this

Twenty-fifth Day of June, 2002

*Attest:*

*Attesting Officer*

JAMES E. ROGAN
*Director of the United States Patent and Trademark Office*